United States Patent [19]

Runnells

[11] Patent Number: 4,993,057
[45] Date of Patent: Feb. 12, 1991

[54] X-RAY TUBE HEAD ASSEMBLY WITH STERILIZABLE HANDLE

[75] Inventor: Robert R. Runnells, Kaysville, Utah

[73] Assignee: MDT Corporation, Torrance, Calif.

[21] Appl. No.: 429,400

[22] Filed: Oct. 31, 1989

[51] Int. Cl.5 .............................................. H05G 1/02
[52] U.S. Cl. ..................................... 378/197; 378/193
[58] Field of Search ............... 378/168, 169, 170, 193, 378/195, 196, 197, 198, 189, 190, 191

[56] References Cited

U.S. PATENT DOCUMENTS

| | | |
|---|---|---|
| D. 279,611 | 7/1985 | Peeler . |
| D. 289,206 | 4/1987 | Scoville et al. . |
| 2,968,732 | 1/1961 | Foderaro ............................. 378/197 |
| 4,104,530 | 8/1978 | Weiss .................................... 378/168 |
| 4,844,252 | 7/1989 | Barron et al. . |

Primary Examiner—Craig E. Church
Attorney, Agent, or Firm—Trask, Britt & Rossa

[57] ABSTRACT

A sterilizable removable handle is provided in associated with an X-ray tube head assembly to permit manipulation of the assembly within a sterile field while avoiding contamination of an operator's hand.

8 Claims, 2 Drawing Sheets

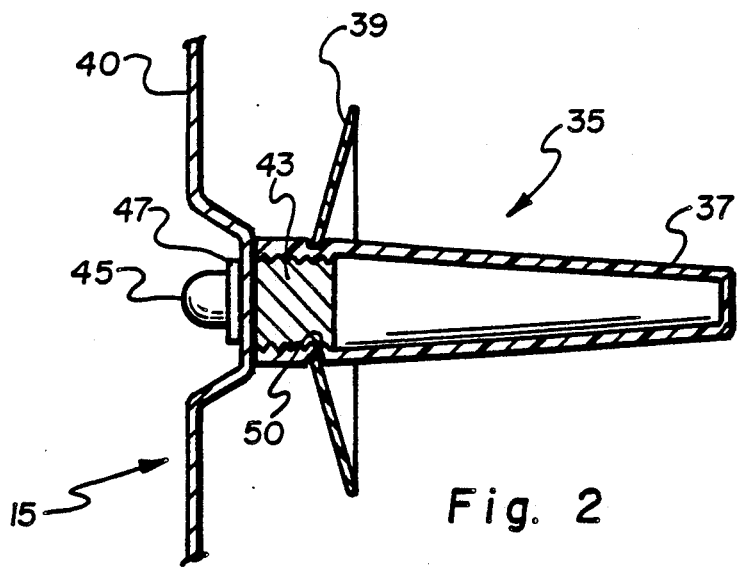
Fig. 2
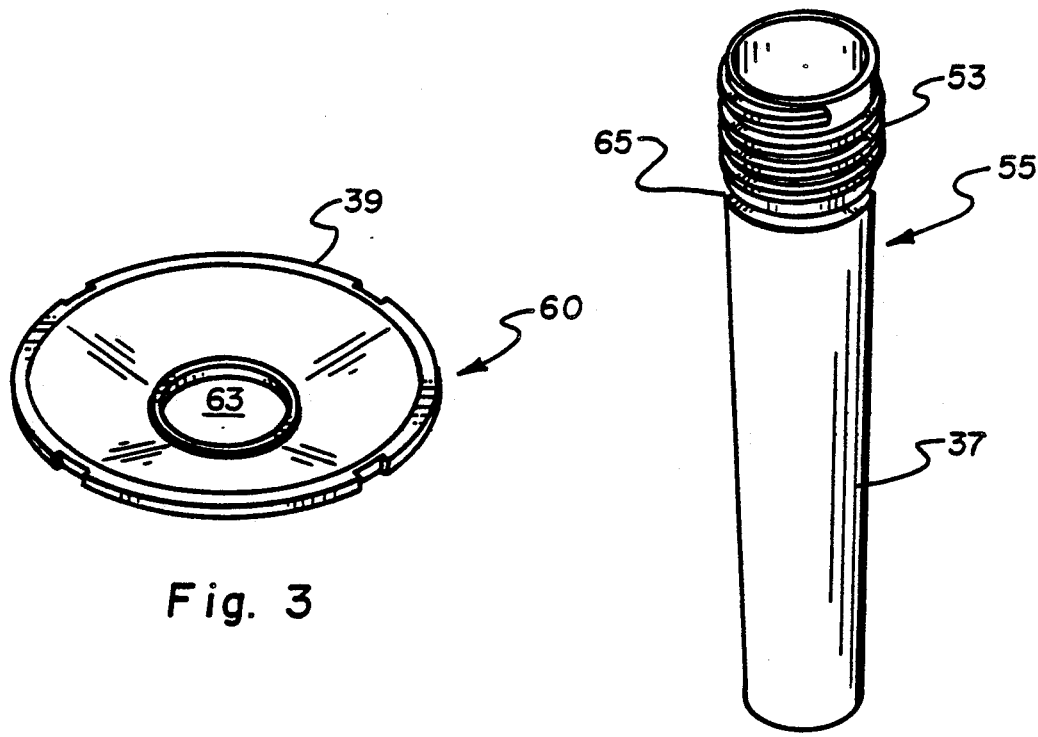
Fig. 3
Fig. 4

X-RAY TUBE HEAD ASSEMBLY WITH STERILIZABLE HANDLE

BACKGROUND OF THE INVENTION

1. Field

This invention relates to X-ray machines and is particularly directed to X-ray tube head assemblies suspended on structures permitting the positioning of the beam emitting device within a sterile field. Specifically, it provides a removable, sterilizable handle in combination with such tube head assemblies.

2. State of the Art

A class of X-ray machines has evolved for use in situations requiring manipulation of the tube head assembly within a sterile field. Notable among these machines are those used in dental practices, although similar machines requiring mobility of the tube head assembly within the sterile area are in use in the practices of medicine and veterinary medicine. It is not generally feasible to maintain the entire X-ray apparatus completely sterile during a procedure. Thus, if the X-ray tube head assembly is to be moved during a procedure, it must ordinarily be moved by non-sterile personnel who may not intrude into the sterile area. If sterile personnel come into contact with the non-sterile tube head assembly, procedures must be followed to reestablish the required sterility. For example, it may be required for an attendant who has readjusted the positioning of the X-ray apparatus to re-glove after each such manipulation. Such procedures are time consuming and wasteful. They also present a substantial risk of inadvertent contamination.

In four-handed dentistry procedures particularly, it would be a great convenience if the X-ray tube head assembly could be manipulated by the dental assistant without compromising the sterility of the hands of the assistant. Frequent manipulations may be required during procedures which require the dental assistant to otherwise intrude into the sterile field. Re-gloving and other precautionary procedures are disruptive and distracting.

Removable sterilizable handles or disposable sterile handles have been used previously in connection with lighting fixtures used in operatories. Examples of such handles are disclosed by U.S. Design Pat. Nos. D 279,611 and 289,206, for example, as well as by U.S. Pat. No. 4,844,252.

There remains a need for a sterilizable mechanism for isolating an operator's hand from contact with the non-sterile housing of a tube head assembly while it is manipulated within the sterile field.

SUMMARY OF THE INVENTION

This invention provides a combination which satisfies the need for an X-ray tube head assembly which can be manipulated within a sterile field without fear of contamination. In general, the combination includes an X-ray tube head assembly comprising a housing with a front surface through which an X-ray beam is emitted, as for example, through a cone. A structural arrangement carries the tube head assembly at a remote location from an anchoring point. A typical such structural arrangement includes folding or scissored arms connected by pivot and swivel linkages, or other means, so that the position of the housing and the orientation of its front surface may be adjusted. For example, in a dental operatory it may be necessary to manipulate the front of the tube head assembly from the left side of the patient to the right side of the patient and to various attitudes at either side, or the front of the patient's jaw.

A handle-mounting structure is carried by the housing in non-interfering relation with respect to the front surface. This structure may be anywhere on the housing, but as a practical matter it is generally preferred at the rear of the housing directly opposite the cone. This location avoids interference with other structural components carried by the tube head assembly and its structural support system. A removable handle element is releasably coupled to the handle-mounting structure with the mounting structure and handle being mutually adapted to couple and decouple from each other. The removable handle may be fashioned as a sterilizable element. It may then be used repeatedly following sterilizations. Alternatively, it may be a pre-sterilized, disposable element which can be discarded once a procedure is completed or in the event of inadvertent contamination during a procedure.

The mounting structure conveniently comprises a post element extending from the housing (preferably at its rear) with the post constituting a first coupling means. The removable handle has a grip section and a coupling section. The coupling section constitutes a second coupling means adapted for coupling and decoupling from the post. In most instances, the post will be provided with male threads at its distal end, and the handle element will be provided with female threads at its proximal end.

It is important for the removable handle to include a guard section at its proximal end adjacent the grip section; that is, in the proximity of the post element. The guard section isolates a hand clasping the grip section from the housing. In this way, contamination of both the hand and the handle by the non-sterile housing is avoided. The guard section may be configured in various ways to facilitate isolation. One embodiment of the invention utilizes a guard section in the form of a slightly dished flange circumscribing the handle body.

As presently preferred, the handle element includes an approximately prismatic body member which includes the grip section at its distal end and the coupling means associated with the handle at its proximal end. The guard then comprises an annular flange member usually of approximately cylindrical disk configuration circumscribing the body member. An ideal body member is shaped approximately as a truncated cone being somewhat tapered from the flange or guard member to its distal end. Of course, the body member may be approximately cylindrical or present a polygonal cross-sectional configuration. In any event, the flange should circumscribe the body member and be of sufficient width to avoid inadvertent contact of the housing by an assistant's hand clasping the handle at its grip portion.

BRIEF DESCRIPTION OF THE DRAWINGS

In the drawings which illustrate what is presently regarded as the best mode for carrying out the invention.

FIG. 2 is a fragmentary cross-sectional view illustrating a portion of the housing and handle elements comprising this invention;

FIG. 3 is a perspective view of a flange member of the handle of FIG. 2; and

FIG. 4 is a perspective view of a body member of the handle element of FIG. 2.

DESCRIPTION OF THE ILLUSTRATED EMBODIMENTS

Figure 1:
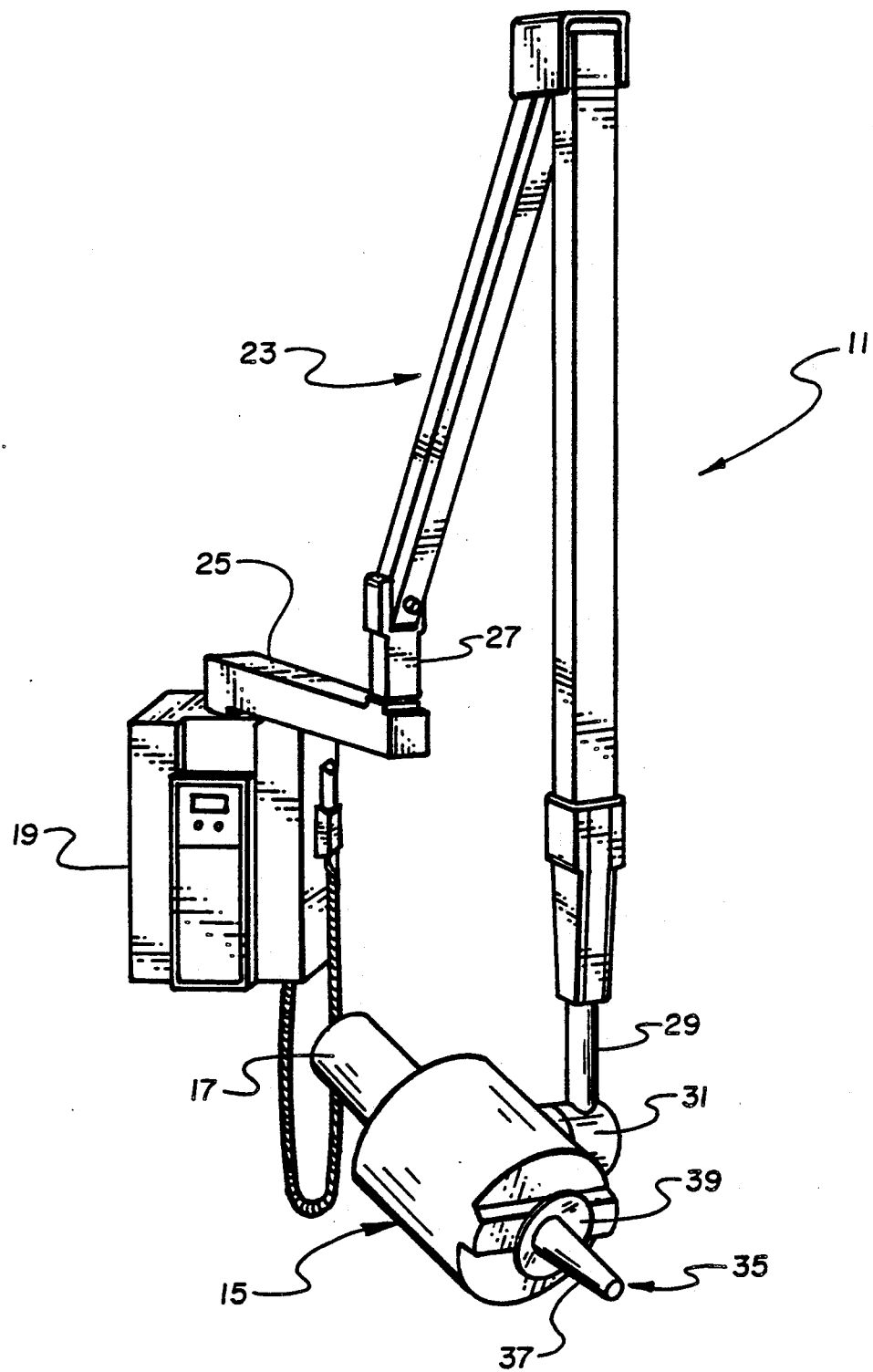
FIG. 1 is a pictorial view of an X-ray machine with a traveling tube head assembly constructed in accordance with this invention.

As best illustrated by FIG. 1, a typical X-ray machine with which this invention finds application, designated generally 11, includes a tube head assembly, designated generally 15, which carries a cone 17 or other beam-limiting device which in use is positioned in the vicinity of a patient's head. The tube head assembly 15 is suspended from a wall-mounted, control panel housing 19 by means of folding arms designated generally 23. The folding arms are suspended from a pivoting arm 25 by means of a swivel pivot connection, while a rotating shaft 29 connects the folding arms 23 to the tube head assembly 15 through a pivot connection 31. The overall structure, as illustrated, permits extensive manipulation of the tube head assembly 15 to position the cone 17 as desired during a dental procedure.

Manipulation of the tube head assembly 15 is accomplished by means of the handle, designated generally 35, shown. The handle includes a grip section 37 and a guard member 39. As best shown by FIG. 2, a rear portion of the housing 40 of the tube head assembly 15 carries a shaft 43 which is fastened by means of nut 45 and oil seal 47 as shown. Threads 50 carried at the distal end of the shaft 43 constitute a first coupling means which is mutually adapted to threads 53 carried in a well at the proximal end of the handle body member designated generally 55 (FIG. 4). The guard 39 may be a separate flange member designated generally 60 (FIG. 3) structured as a cylindrical annulus having a central aperture 63 adapted to form a snap-fit connection with corresponding grooves 65 in the handle member 55.

The handles, including both the body member 55 and flange member 60, may be of unitary construction of the type disclosed by Design Patent 289,206, the disclosure of which is incorporated by reference as illustrative of a handle element suitable for incorporation as a structural member of this invention, or it may be of two-piece construction, as illustrated by U.S. Pat. No. 4,844,252, the disclosure which is incorporated herein by reference as a further example of a handle element which may be incorporated as a component of this invention.

In either event, the handle members may be sterilizable for repeated use or they may be provided separately as sterilized disposable components of the invention defined by the appended claims.

Reference herein to details of the illustrated embodiment is not intended to restrict the scope of the appended claims which themselves recite those details regarded as important to the invention.

What is claimed:

1. In combination, an X-ray tube head assembly comprising a housing with a front surface through which an X-ray beam is emitted;

a structural support system anchored at a first location and carrying said tube head assembly at a remote location, said structural support system constituting means whereby the position of said assembly and the orientation of said front surface may be adjusted;

mounting structure carried by said housing in non-interfering relation with respect to said front surface; and a removable handle element releasably coupled to said mounting structure;

said mounting structure and handle being mutually adapted to couple with and decouple from each other; and said handle constituting means whereby said structural support system may be operated to effect changes in the spatial location of said assembly and the orientation of said front surface.

2. A combination according to claim 1 wherein said mounting structure comprises a post element extending from said housing, said post element constituting first coupling means; and said removable handle has a grip section and a coupling section, said coupling section constituting second coupling means; said first and second coupling means being mutually adapted for coupling with and decoupling from each other.

3. A combination according to claim 2, wherein said removable handle includes a guard section at the end of said grip section closest said post element; said guard section being configured to isolate a hand clasping said grip section from said housing.

4. A combination according to claim 2, wherein said first coupling means carries first screw threads and said second coupling means carries second screw threads, said first and said second screw threads together forming a male/female threaded coupling.

5. A combination according to claim 4, wherein said first coupling means comprises male threads at the distal end of said post element; and said second coupling means comprises female threads in a well carried by the proximal end of said handle element opposite said grip section from said guard.

6. A combination according to claim 4, wherein said handle element includes an approximately prismatic body member including said grip section at its distal end and said second coupling means at its proximal end and said guard comprises an approximately cylindrical disk flange member circumscribing said body member.

7. A combination according to claim 6, wherein said body member is shaped approximately as a truncated cone.

8. A combination according to claim 6, wherein said flange member is annular with a central aperture adjusted to releasably engage the outer surface of said body member.

* * * * *